United States Patent
Glines et al.

(10) Patent No.: US 6,190,311 B1
(45) Date of Patent: *Feb. 20, 2001

(54) RETRACTOR AND INSTRUMENT PLATFORM FOR A LESS INVASIVE CARDIOVASCULAR SURGICAL PROCEDURE

(75) Inventors: Robert C. Glines, Cameron Park; Ivan Sepetka, Los Altos, both of CA (US)

(73) Assignee: Cardiothoracic Systems, Inc., Cupertino, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/850,150

(22) Filed: May 2, 1997

(51) Int. Cl.⁷ .................................................. A61B 1/30
(52) U.S. Cl. ........................................ 600/208; 600/215
(58) Field of Search .................................. 600/208, 215

(56) References Cited

U.S. PATENT DOCUMENTS

| | | | |
|---|---|---|---|
| Re. 34,150 | 12/1992 | Santilli et al. | 128/20 |
| 4,049,000 | 9/1977 | Williams | 128/276 |
| 4,421,107 | * 12/1983 | Estes et al. | 600/215 |
| 4,434,791 | 3/1984 | Darnell | 128/20 |
| 4,627,421 | 12/1986 | Symbas et al. | 128/20 |
| 4,702,230 | 10/1987 | Pelta | 128/20 |
| 4,726,356 | 2/1988 | Santilli et al. | 128/20 |
| 4,747,395 | 5/1988 | Brief | 128/20 |
| 4,829,985 | 5/1989 | Couetil | 128/20 |
| 4,852,552 | 8/1989 | Chaux | 128/20 |
| 4,865,019 | 9/1989 | Phillips | 128/20 |
| 4,884,559 | 12/1989 | Collins | 128/17 |
| 4,971,037 | 11/1990 | Pelta | 128/20 |
| 4,993,862 | 2/1991 | Pelta | 403/59 |
| 5,025,779 | 6/1991 | Bugge | 128/20 |
| 5,052,373 | 10/1991 | Michelson | 128/20 |
| 5,159,921 | * 11/1992 | Hoover | 600/208 |
| 5,167,223 | 12/1992 | Koros et al. | 128/20 |
| 5,520,610 | * 5/1996 | Giglio | 600/208 |

FOREIGN PATENT DOCUMENTS

| | | | |
|---|---|---|---|
| 0 803 228 A1 | 10/1997 | (EP) | A61B/17/02 |
| 168216 | 9/1921 | (GB) . | |
| 2 267 | 12/1993 | (GB) . | |
| WO97/3251 | 9/1997 | (WO) . | |

OTHER PUBLICATIONS

Pilling Surgical Instruments, A Rusch International Company, Brochure.

Delacroix–Chevalier Surgical Instruments, IMA Savings Packages Brochure.

Ancalmo, N., and J.L. Ochsner: A Modified Sternal Retractor, Ann. Thorac. Surg. 21 (1976) 174.

Beg, R.A., H. Naraghipour, E.B. Kay, and P. Rullo: Internal Mammary Retractor, Ann. Thorac. Surg. 39 (1985) 286–287.

(List continued on next page.)

*Primary Examiner*—Gary Jackson
(74) *Attorney, Agent, or Firm*—Bozicevic, Field & Francis LLP; Alan W. Cannon

(57) ABSTRACT

An instrument platform and retractor, for holding and organizing cannulas, instruments and sutures during a surgical procedure, wherein the instrument platform has a platform body which is mountable to the retractor and includes a central opening and cannula notches formed therein adjacent to the central opening for securing cannulas during a surgical procedure. The platform body also includes suture grips and instrument mounts for securing surgical instruments and sutures during a surgical procedure. The retractor includes a pair of blades and a spreader mechanism detachably mounted to blade arms.

33 Claims, 6 Drawing Sheets

OTHER PUBLICATIONS

Chaux, A., and C. Blanche: A New Concept in Sternal Retraction: Applications for Internal Mammary Artery Dissection and Valve Replacement, Ann. Thorac. Surg. 42 (1986) 473–474.

McKeown, P.P., J. Crew, E.S. Hanna, and R. Jones: A Modified Sternal Retractor for Exposure of the Internal Mammary Artery, Ann. Thorac. Surg. 32 (1981) 619.

Vincent, J.G.: A Compact Single Post Interanl Mammary Artery Dissection Retractor, Eur. J. Cardio–Thor. Surg. 3 (1989) 276–277.

Campalani, G., M.D., et al., A new self–retaining internal mammary artery retractor, J. Cardiovas. Surg. 28, 1987.

Pittman, John, M.D., et al., Improved Visualization of the Internal Mammary Artery With a New Retractor System, Ann. Thorac. Surg. (1989;48:869–70).

Angelini, G. D., M.D., et al., A Fiber–Optic Retractor for Harvesting the Internal Mammary Artery, Ann. Thorac. Surg. (1990;50:314–5).

Phillips, Steven J., M.D., et al., A versatile retractor for use in harvesting the internal mammary artery and performing standard cardiac operations, J. Thorac. Cardiovasc. Surg. (1989;97:633–5).

Itoh, Toshiaki, M.D., et al., New Modification of a Mammary Artery Retractor, Ann. Thorac. Surg. (1994;57:1670–1).

Roux, D., M.D. et al., Internal mammary artery dissection: A three dimensional sternal retractor, J. Cardiovasc. Surg. (1989;30:996–7).

USSC Cardiovascular Thora–Life™, United States Surgical Corporation, Norwalk, Connecticut, Product Brochure.

* cited by examiner

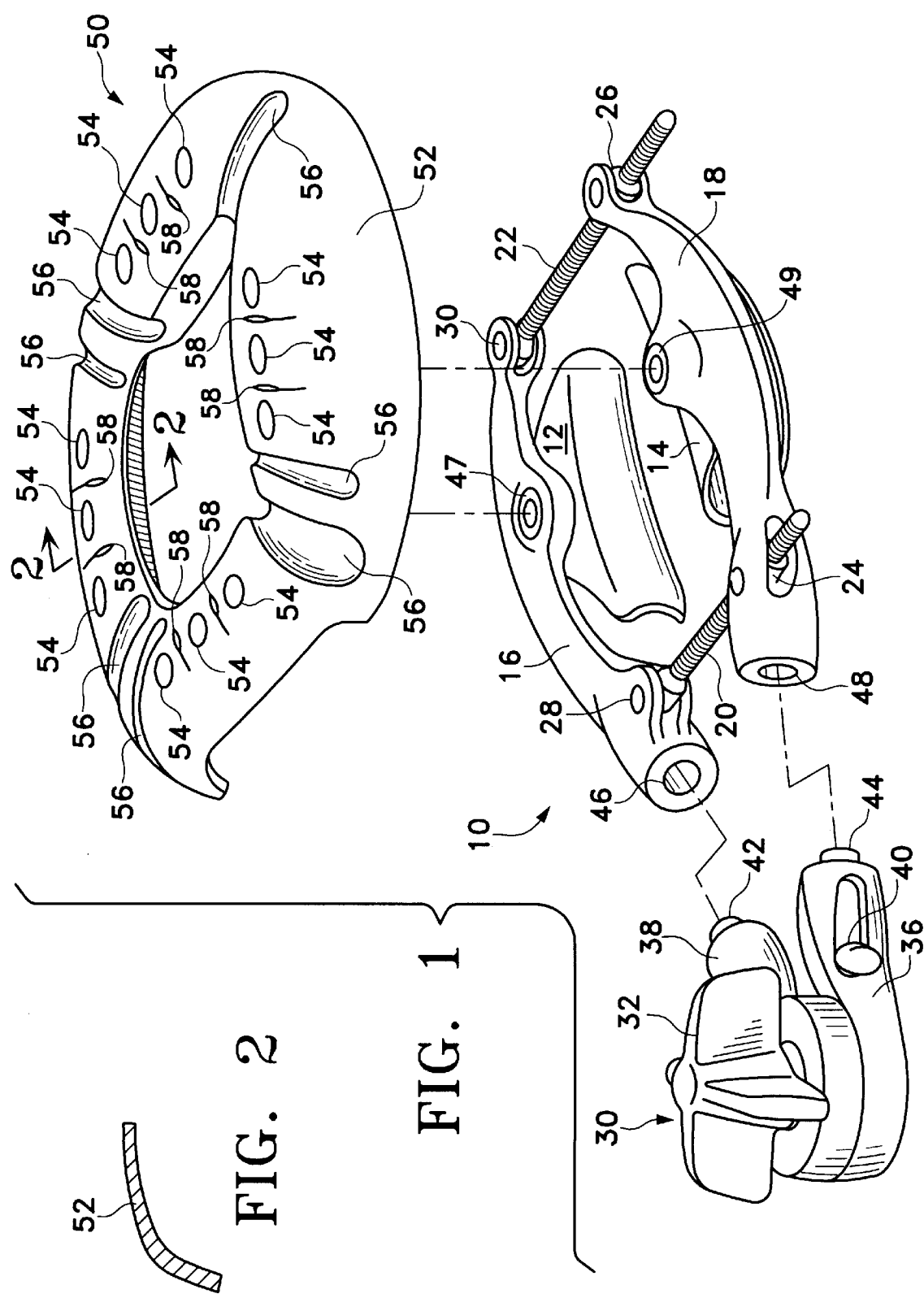

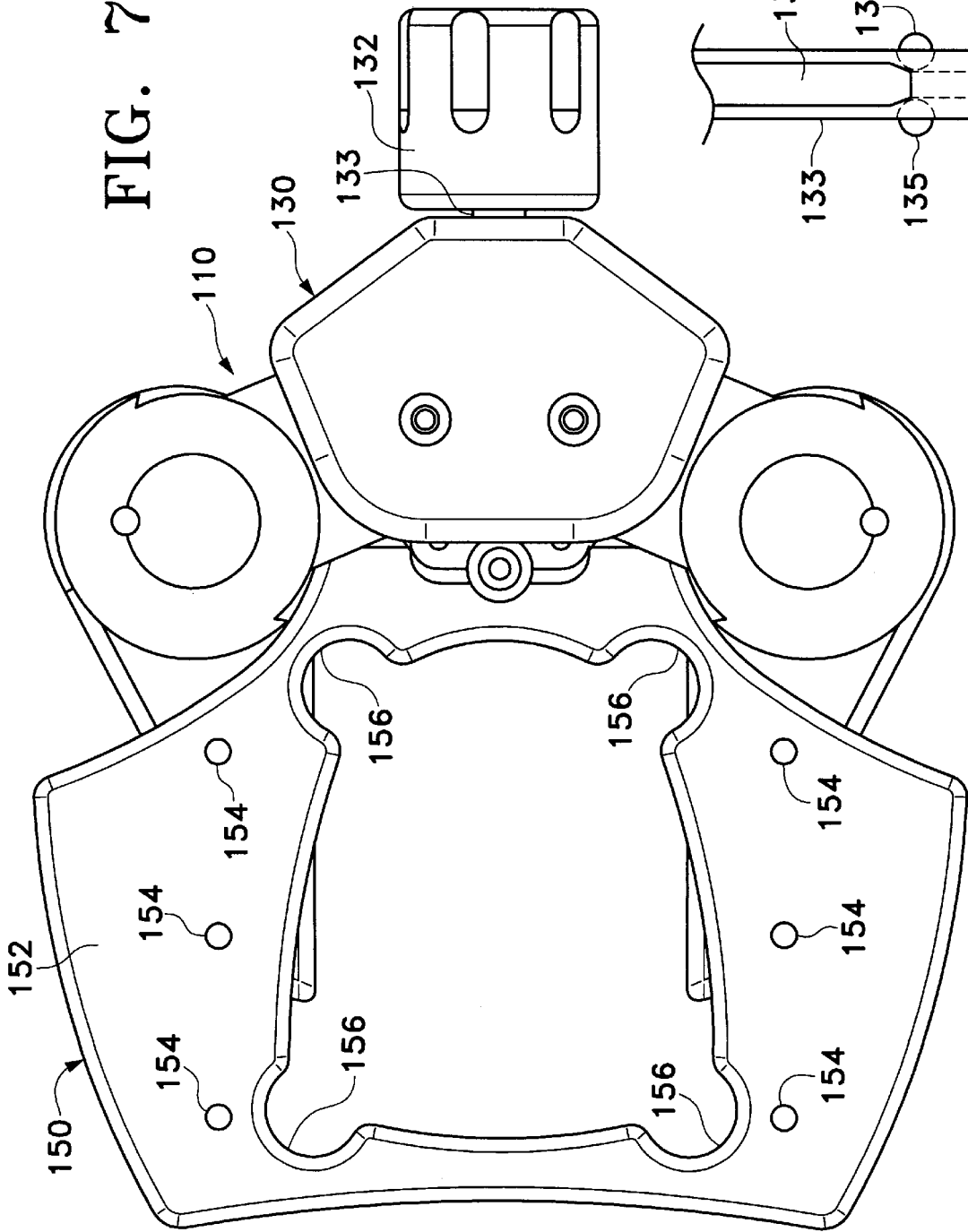
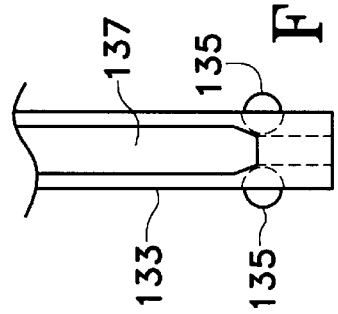

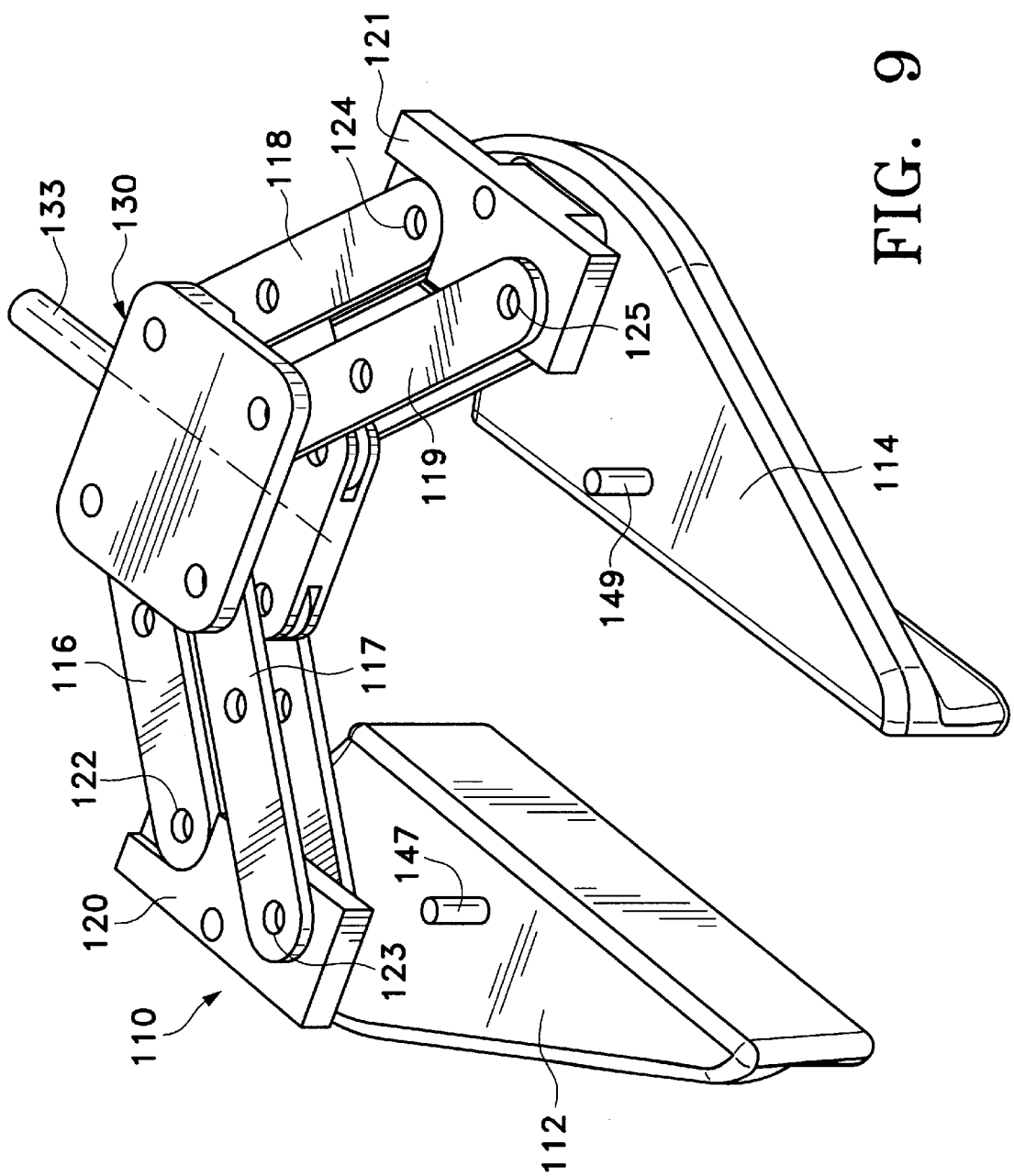

RETRACTOR AND INSTRUMENT PLATFORM FOR A LESS INVASIVE CARDIOVASCULAR SURGICAL PROCEDURE

FIELD OF THE INVENTION

This invention relates to apparatuses for and methods of cardiovascular surgery, and more particularly, to a retractor and instrument platform that facilitates access to the thoracic cavity and the performance of a less invasive cardiovascular surgical procedure.

BACKGROUND OF THE INVENTION

Diseases of the cardiovascular system affect millions of people each year and are a leading cause of death in the United States and throughout the world. The cost to society from such diseases is enormous, both in terms of lives lost and the cost of treating cardiac diseased patients through surgery. It is well known that certain of these diseases may result in disorders of the cardiac valves. Some of these diseases may result in endocarditis, which is an inflammation of the endocardium or the membrane lining the heart, while other diseases, such as rheumatic fever, may cause shrinkage or separation of the orifice of a valve. The resulting defects in the cardiac valves, which include the narrowing of the valve commisores (valvular stenosis) and/ or the defective closing of the valve (valvular insufficiency), tend to hinder the normal operation of the heart by causing an accumulation of blood in a heart cavity or regurgitation of blood past the valve. In many cases, complete valve replacement is required because of damage caused to heart muscle by prolonged valvular stenosis or insufficiency.

Although replacement of heart valves has become relatively common, i.e., as many as 80,000 heart valve prostheses are implanted in the United States alone, the procedure is lengthy and traumatic, and in many instances, the surgical technique requires breaking of bones. In a conventional heart valve prosthesis procedure, the surgeon typically performs a sternotomy, cuts off the blood to the heart and then stops the heart from beating in order to replace the valve. Thus, in order to perform this procedure, the surgeon makes a long incision down the middle of the chest, saws through the entire length of the sternum, spreads the two halves of the sternum apart, and then performs several procedures necessary to stop the heart and attach the patient to a cardiopulmonary bypass machine to continue the circulation of oxygenated blood to the rest of the body while the cardiac valve is being replaced.

During the heart valve replacement procedure, the pericardium is opened to expose the heart. To improve exposure of the heart, sutures are typically fixed to the edges of the pericardial opening to retract the opening and then tied to the patient's chest to secure the sutures. The heart is then cannulated to establish vents and cardiopulmonary bypass (CPB), and to provide cardioplegia delivery. Once CPB is established, the heart is isolated by clamping the aorta and a cardioplegia solution is infused to arrest the heart. In the instance of aortic or mitral valve replacement, an aortotomy or atriotomy is performed to expose the defective cardiac valve. After the valve is excised, a valve prosthesis can be implanted.

To implant the valve prosthesis, sutures are placed in the annulus and tagged. While keeping the sutures organized, which can prove to be a complicated task, the sutures are placed in the sewing ring of the valve prosthesis. The valve prosthesis is then seated and the sutures are tied to secure the valve prosthesis in place. To complete the procedure, the aortotomy or atriotomy is closed, the heart is vented and resuscitated, the vents and other cannulas are removed, the incisions are closed, and then the sternotomy is closed.

As noted above, the conventional procedure is lengthy and traumatic. The typical sternotomy is invasive and results in prolonged and difficult recovery. The conventional procedure also tends to be complicated by the presence of a large number of instruments, sutures and cannulas that potentially clutter the access to the heart and by the need to quickly place sutures in the annulus and valve prosthesis while keeping the sutures organized. Thus, it would be desirable to provide an apparatus that facilitates a less invasive procedure, that facilitates access to and exposure of the heart, and that facilitates the organization and placement of sutures as well as instruments and cannulas during the surgical procedure.

SUMMARY OF THE INVENTION

The wound retractor and instrument platform of the present invention serve to facilitate the performance of a less invasive and simplified surgical procedure while facilitating access to and exposure of the heart and the organization and placement of sutures, cannulas and surgical instruments. The retractor preferably has a pair of blades detachably connected to first and second blade arms which are connected to a spreader mechanism. The spreader mechanism, or portion thereof, is preferably detachable from the first and second blade arms. The instrument platform is mountable to the retractor and preferably has a platform body that includes a central opening and a plurality of cannula notches or slots formed therein adjacent to the central opening. Cannulas, used during a surgical procedure, can advantageously be secured in a notch or slot and be held in a position that tends not to obstruct a surgeon's access. The platform body also preferably includes a plurality of suture grips and instrument mounts used to hold sutures and surgical instruments in place during the surgical procedure, and advantageously keep the sutures organized during the surgical procedure.

In operation, the retractor is preferably used to create an opening in the body of a patient. Once the opening in the body cavity is created, the instrument platform is mounted to the retractor and the surgical procedure can be performed through the central opening of the instrument platform into the opening in the patient's body. The cannulas, instruments and sutures used during the surgical procedure are advantageously held in place by the instrument platform so as not to obstruct the surgeon's access to the opening in the patient's body.

An object of this invention is to provide an improved instrument platform and retractor assembly.

Further objects and advantages of the present invention will become apparent from a consideration of the drawings and ensuing description.

BRIEF DESCRIPTION OF THE DRAWINGS

FIG. 1 is an exploded isometric view of a novel wound retractor and instrument platform of the present invention.

FIG. 2 is a partial cross-sectional view of the instrument platform taken along line 2—2 in FIG. 1.

FIG. 7 is a top view of an instrument platform mounted on an alternative embodiment of the wound retractor of the present invention.

FIG. 8 is a partial profile view of a drive shaft of a spreader mechanism of the wound retractor shown in FIG. 7.

FIG. 9 is a partial isometric view of the retractor shown in FIG. 7 less an actuator knob of the spreader mechanism.

DESCRIPTION OF THE PREFERRED EMBODIMENT

Figure 3:
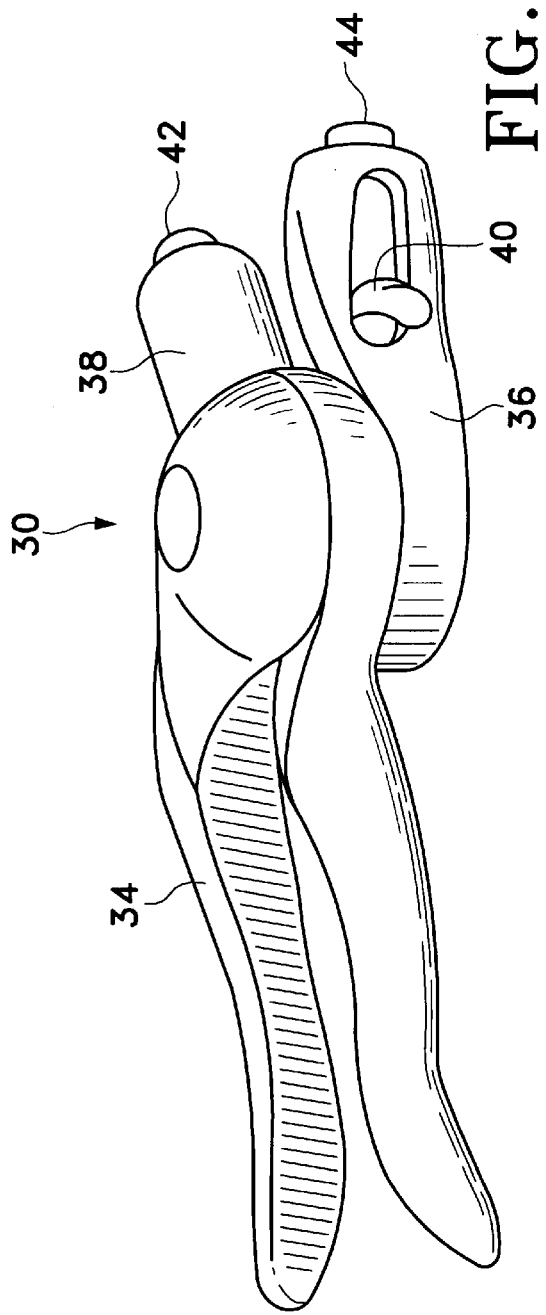
FIG. 3 is an isometric view of an alternate spreader mechanism for the wound retractor shown in FIG. 1.

Referring now in detail to the figures, therein illustrated is a novel wound retractor 10 and an instrument platform 50 which tend to facilitate and simplify less invasive methods for surgical procedures. For exemplary purposes only, the operational use of the wound retractor 10 and instrument platform 50 of the present invention will be discussed as the use relates to valve replacement procedures. However, it will be understood by those skilled in the art that the wound retractor 10 and instrument platform 50 of the present invention could be used to perform a variety of surgical procedures within the thoracic cavity, such as a coronary artery bypass graph procedure, a cardiac heart valve repair procedure, a heart transplant procedure, to name a few, and other laparoscopic or general procedures in other areas of the body.

In FIG. 1, the wound retractor 10 is shown to include retractor blades 12 and 14 attached to a pair of blade arms 16 and 18. The blades 12 and 14 are detachably mounted to the blade arms 16 and 18 and, thus, are interchangeable depending on the type of procedure used to access the thoracic cavity, e.g., a parasternal approach, a mini-thoracotomy, or a mini-sternotomy. Depending on which approach is used, the blades 12 and 14 may be curved or straight, or a combination thereof.

The blade arms 16 and 18 are operably interconnected to one another by ratcheted shafts 20 and 22. The shafts 20 and 22 are pivotally connected to one of the blade arms 16 at pivots 28 and 30, and slidably received in ratchet sleeves 24 and 26 which are pivotally mounted to the other blade arm 18. As the blade arms 16 and 18 are spread apart by a spreader mechanism 30, the ratcheted shafts 20 and 22 and ratchet sleeves 24 and 26 maintain the blade arms 16 and 18 in spaced relation.

The spreader mechanism 30, which includes an actuator knob 32, is operably connected to spreader arms 36 and 38 which are detachably coupled to the blade arms 16 and 18. The spreader arms 36 and 38 include mounting stems 42 and 44 that extend outwardly from the end of the spreader arms 36 and 38. The stems 42 and 44 are slidably received in sockets 46 and 48 that are cut into the ends of the blade arms 16 and 18. A locking mechanism 40 on each spreader arm 36 and 38 (not shown for spreader arm 38) fixedly couples the spreader mechanism 30 to the blade arms 16 and 18. With the spreader mechanism 30 coupled to the blade arms 16 and 18, the knob 32 can be rotated to spread or close the blade arms 16 and 18. Alternatively, the knob 32 of the spreader mechanism 30 can be replaced with a ratchet lever mechanism 34, as shown in FIG. 3, wherein the ratchet lever mechanism 34 can be operated by means of a gripping action to spread or close the blade arms 16 and 18.

It will be understood by those skilled in the art that a number of alternate embodiments of the wound retractor 10. FIGS. 7–9 (discussed below) show an alternate embodiment of a wound retractor 100, while other alternate embodiments of the wound retractor are disclosed in co-pending application Ser. No. 08/787,748, entitled "Access Platform for Internal Mammary Dissection", which is incorporated herein as if set forth in full.

Referring to FIG. 1, the instrument platform 50 of the present invention is detachably mounted to the retractor 10 by bosses 47 and 49 formed on the blade arms 16 and 18. The bosses 47 and 49 snap into recesses or receptacles (not shown) on the underside of the instrument platform 50. The instrument platform 50 includes a shell body 52 with a central opening 51 that substantially matches an opening in the thoracic cavity created by the spreading of the blades 12 and 14 of the wound retractor 10. The shell body 52 is preferably constructed from injected molded plastic. However, as an alternative, it would be advantageous to form the shell body 52 from copper plating or some other material that is malleable, and coat it with an elastomeric material to enable the body 52 to conform to the shape of a patient's chest.

As shown in FIG. 2, the shell body 52 has a generally thin, curvalinear "L"-shaped cross-section. The outer edge of the shell body 52, when in use, is located adjacent to a patient's chest while the portion of the shell body 52 adjacent the central opening 51 is elevated from the patient's chest. This construction creates a space between the patient's chest and the shell body 52 to enable the instrument platform 50 to mount over the blade arms 16 and 18 of the wound retractor 10.

As shown in FIG. 1, the upper surface of the shell body 52 of the instrument platform 50 includes a plurality of cannula notches or slots 56 positioned along the upper surface of the shell body 52 adjacent to the central opening 51 at 90° intervals from one another. The cannula slots 56 are sized to releasably retain cannulae, catheters and other instruments used in surgical procedures. Also included along the surface of the shell body 52 are mounts used to connect a variety of instruments (see FIGS. 4–6). For exemplary purposes only, these mounts are shown as holes 54. It will be understood that a variety of holes, slots, keyed passages, grooves, recesses, protrusions, tabs, bosses, etc., could act as mounts to facilitate the connection of an instrument to the instrument platform.

In addition to the mounts, the shell body 52 includes a plurality of suture grips 58 formed in the surface of the shell body 52. The suture grips 58 include a canyon portion and a narrow slot portion. The canyon and slot portions are preferably formed as elongated V-shaped notches, with the canyon notch being larger and deeper than the notch of the slot portion. In operation, the surgeon quickly locates the suture grip on the platform body at the canyon portion and then wedges the suture into the slot portion. To aid in gripping the suture, a piece of rubber or other material is wedged in the slot portion of the suture grips 58. The suture grips 58 tend to eliminate the need for additional assistants and/or the need to tie sutures to a patient's skin.

Figure 4:
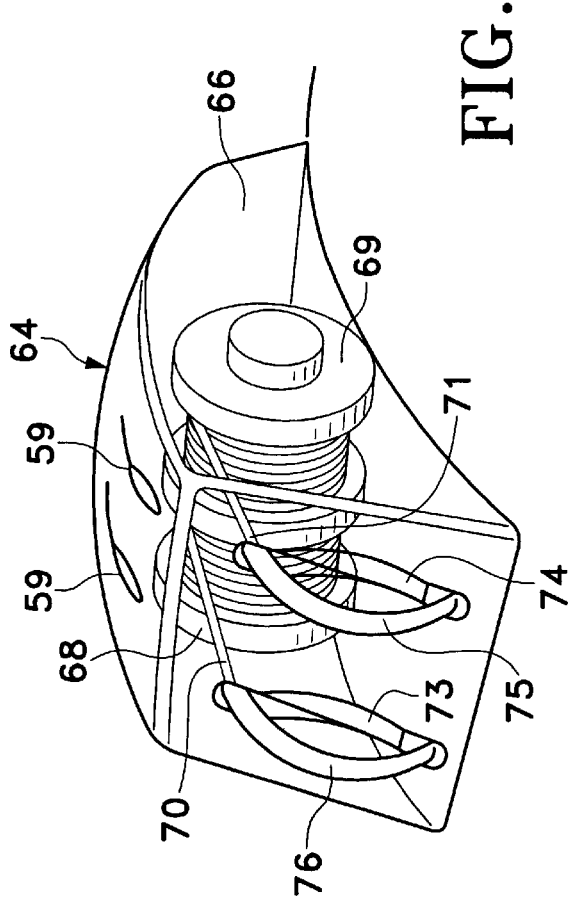
FIG. 4 is an isometric view of a suture spool assembly which is mountable on the instrument platform shown in FIG. 1.

Turning to FIG. 4, a suture spool 64 is shown having spool members 68 and 69 mounted in a housing 66 that is mountable to the shell body 52 of the instrument platform 50 by engaging a mount on the platform body 52. Sutures 70 and 71 are wound about the spool members 68 and 69. Needles 75 and 76 are held in position within needle slots 73 and 74 in the housing 66 and are attached to sutures 70 and 71. The needles 75 and 76 are easily accessible by the surgeon and the sutures 70 and 71 can be drawn out of the suture housing 66 through the needle slots 73 and 74. Optionally, the suture housing 66 may include suture grips 59 formed on the upper surface of the housing 66 to secure the sutures 70 and 71 after they have been placed during a surgical procedure. The mounting of the suture spool 64 on the instrument platform 50 tends to eliminate the need for additional assistants and organization, thus reducing the time it takes to perform the procedure.

In operation, the retractor 10 is assembled by attaching the blades 12 and 14 and the spreader mechanism 30 to the blade arms 16 and 18. With the retractor 10 assembled, the blades 12 and 14 are inserted into an incision. The spreader mechanism 30 is then operated to gently spread the blade arms 16 and 18 apart creating the desired spacing between the blades 12 and 14. Once the desired spacing between the blades 12 and 14 is achieved, the spreader mechanism 30 can be detached from the blade arms 16 and 18 and the instrument platform 50 can be mounted to the retractor 10 and over the blade arms 16 and 18 to perform the desired surgical procedure.

Figure 5:
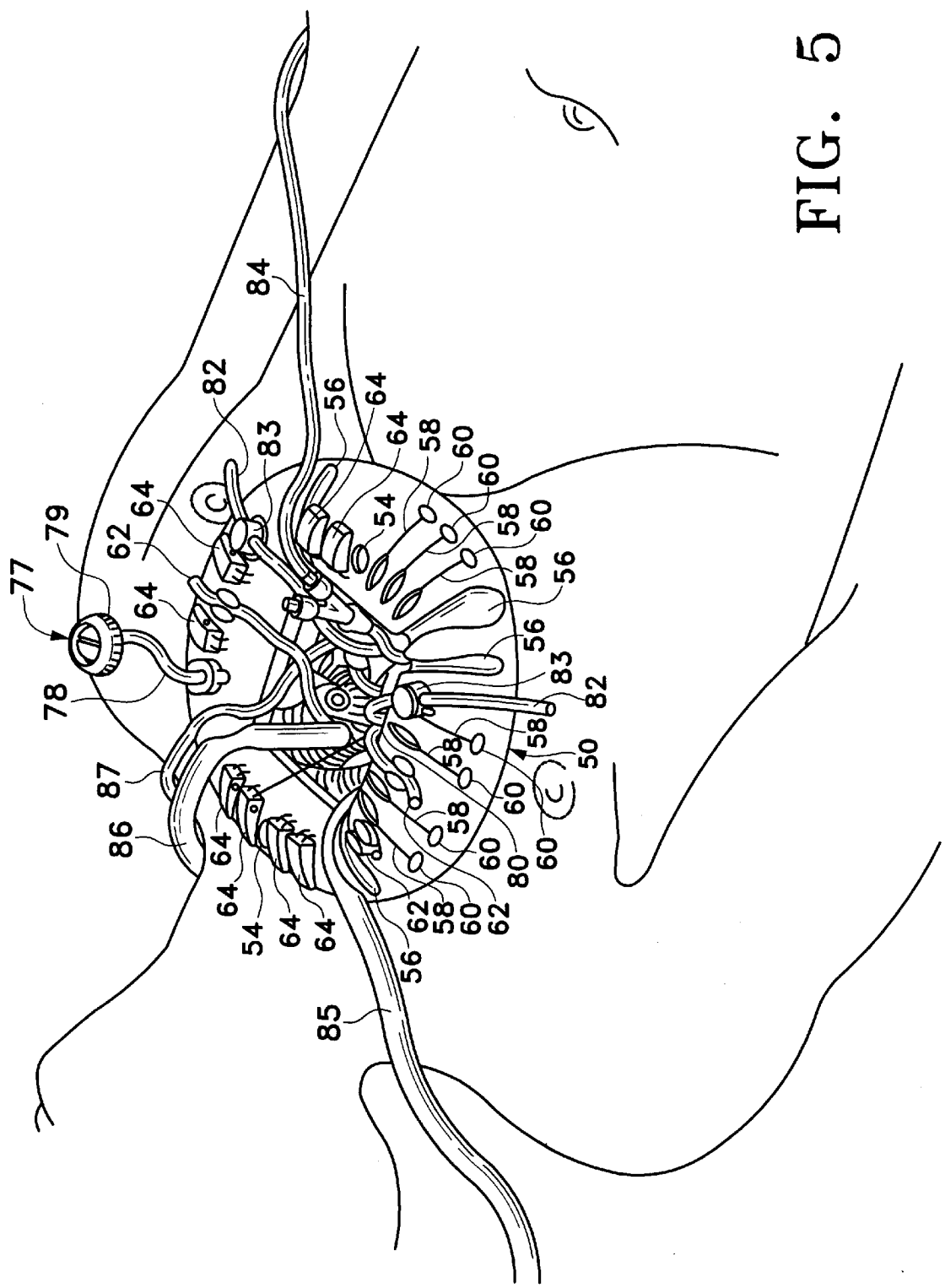
FIG. 5 is an isometric view of the instrument platform shown in an installed position over a mini-sternotomy in the thoracic cavity of a patient during an aortic valve replacement procedure. A plurality of cannulas, instruments and sutures are shown positioned on the instrument platform.

Referring to FIG. 5, the instrument platform 50 is shown in position over a ministernotomy in a patient's chest. The mini-sternotomy advantageously provides less invasive access to the thoracic cavity by making an incision approximately 8 centimeters long somewhere along the sternum and then gently spreading apart only the incised portion of the sternum. With the instrument platform 50 in place over the mini-sternotomy, the surgeon can perform the desired surgical procedure. In regard to FIG. 5, for exemplary purposes only, the use of the instrument platform will be discussed in regard to an aortic valve replacement procedure.

As noted above, an approximately 8 centimeter long incision is made somewhere along the sternum to perform a mini-sternotomy. The blades 12 and 14 of the wound retractor 10 are then secured in place within the incision and gently separated to spread apart the portion of the sternum in which the incision was made. The blade arms 16 and 18 are spread apart until a desired spacing between the blades 12 and 14 is achieved. The spreader mechanism 30 is then detached from the blade arms 16 and 18 and the instrument platform 50 is mounted over or attached to the retractor 10. With the instrument platform in place, the pericardium is opened to expose the heart. To improve exposure, several sutures are placed in the edges of the pericardial opening and fixed in place in the suture grips 58 located on the surface of the instrument platform 50, thus eliminating the need to fix the sutures to the patient's skin. The heart is then cannulated by placing an arterial cannula 86 in the aorta, a two-stage venous cannula 85 in the atrium, a vent catheter 87 in the left ventricle and an antegrade cardioplegia catheter 84 in the aortic root or coronary ostia. The cannulas 84, 85, 86 and 87 are snapped into the cannula slots 56 on the instrument platform 50 and advantageously held in a position so as not to obstruct the surgeon's access to the heart.

Choker grips 62 are provided on the surface of the instrument platform 50 and are used to grip purse-string type sutures used to secure the cannulas 84, 85, 86 and 87 in place. The choker grips 62 are formed from elastomeric tubing and, when secured to the platform, tend to eliminate the need for a hemostat and, thus, tend to eliminate any obstructions associated with the use of a hemostat and save time in securing the purse string sutures. In operation, for example, with regard to cannulating the aorta, a purse string suture is placed in the tissue of the aorta. The tissue of the aorta surrounded by the purse string suture is pierced and the cannula is fitted in the resulting hole. The free ends of the purse string suture are passed through a choker grip and then cinched tight around the cannula to secure it in place. The choker grip and suture are then wedged into a suture grip to maintain the tension on the purse string suture around the cannula.

After cannulation is completed, cardiopulmonary bypass (CPB) is established utilizing the arterial and venous cannulas 85 and 86. Next, the aorta is cross-clamped utilizing an aortic clamp 80, shown with its handle removed, and a cardioplegic solution is infused through the anti-grade cardioplegia catheter 84 to arrest the heart.

Once the heart is arrested, an aortotomy is performed to expose the aortic valve. Aortic retractors used to retract the aorta and other tissues extend from the platform 50 on malleable shafts 82 into the heart. The malleable shafts 82 are slidably received in connectors 83 which engage a mount on the platform 50. By mounting an aortic retractor to the platform 50, the need for additional sets of hands in the surgeon's working space to perform retraction of the aorta or other tissue tends to be eliminated.

With the aorta retracted, the aortic valve leaflets are excised. Sutures from the suture spools 64, or individual sutures, are then placed in the valve annulus and retained by suture grips on the housing 66 of the suture spools 64 or suture grips 58 on the surface of the instrument platform 50. The suture grips 58 tend to assist the surgeon in organizing the sutures that are placed in the annulus. Tags 60 can be formed on the surface of the platform 50 to identify the suture in the associated suture grip 58.

A valve holder 78 is mounted on the platform 50 by a connector that engages a mount. To assist in moving the valve holder 78 in and out of the retracted space in the thoracic cavity, the stem of the valve holder 78 may be hingedly connected to the connector and/or constructed from a malleable material. The valve holder 78 includes a connector that mates with the cuff or mounting mechanism 79 of the valve prosthesis 77. With the valve prosthesis 77 mounted on the valve holder 78, the valve prosthesis 77 can be positioned adjacent the annulus in the heart to place sutures in its cuff 79. After the sutures are placed in the cuff 79, the valve prothesis 77 is seated in the annulus and the sutures are tied to secure the valve prosthesis 77 in place. With the valve prosthesis 77 implanted, the aortotomy is closed, air is evacuated from the heart through the vent 87, the heart is resuscitated, and the catheters and cannulas 84, 85, 86 and 87 are removed and the corresponding incisions are closed. Next, the pericardium is closed, the instrument platform 50 is removed, the spreading mechanism is attached to the blade arms 16 and 18, and the blades 12 and 14 are returned to a closed position. Once in the closed position, the blades 12 and 14 are removed and the sternotomy is closed.

Figure 6:
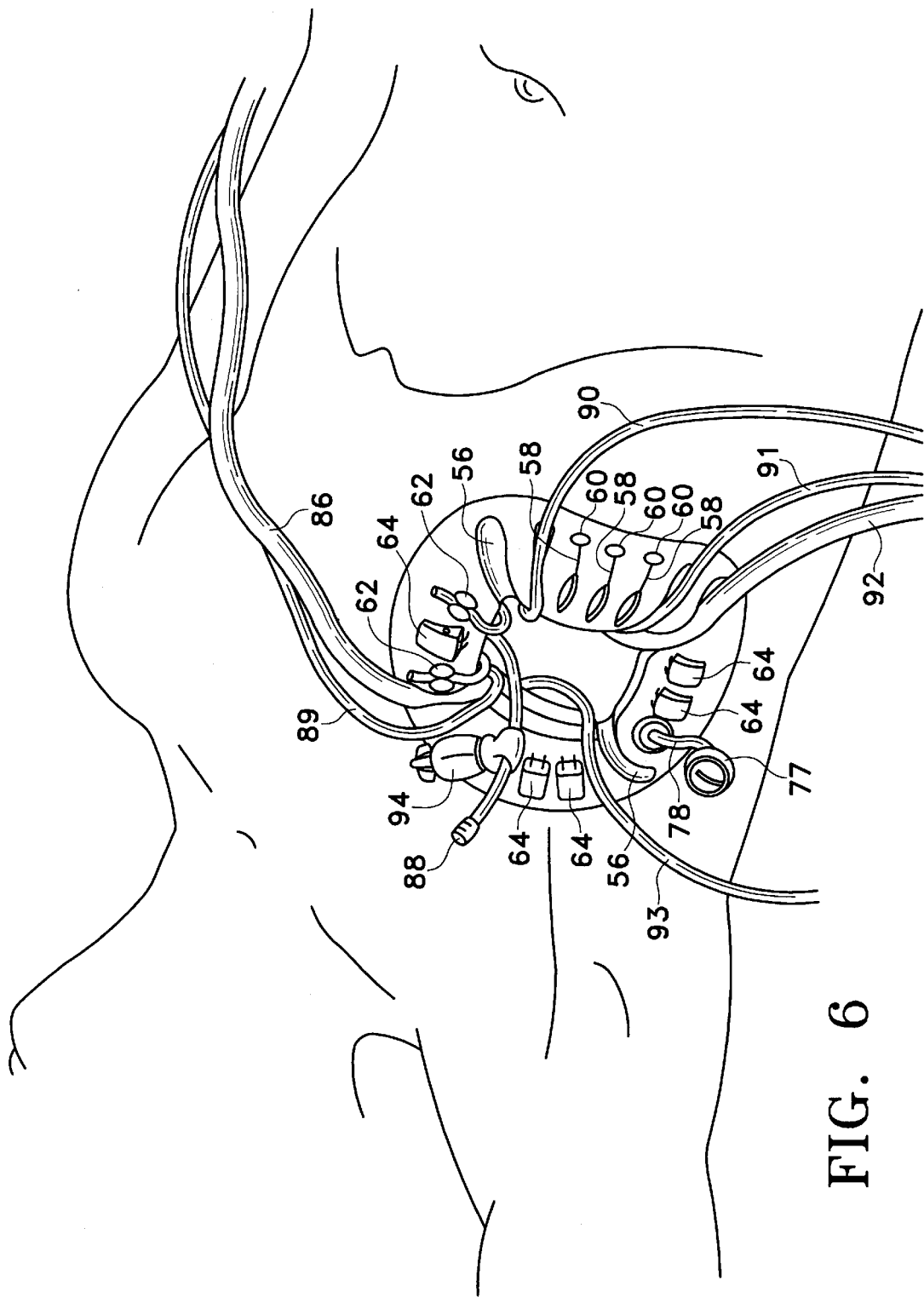
FIG. 6 is an isometric view of the instrument platform shown in an installed position over a mini-thoracotomy in the thoracic cavity of a patient during a mitral valve replacement procedure. A plurality of cannulas, instruments and sutures are shown positioned on the instrument platform.

As shown in FIG. 6, the retractor 10 and instrument platform 50 can similarly be used in a mitral valve replacement procedure. The instrument platform 50 is shown conforming to the shape of the patient's chest and in place over a mini-thoracotomy. With the instrument platform 50 in place, and with the mini-thoracotomy already performed, the pericardium is opened to expose the heart. To improve the exposure, sutures are placed in the edges of the pericardial opening and fixed in the suture grips 58 on the platform body 52. The heart is then cannulated and vented by installing an vent catheter 89 in the left atrium or ventricle, an arterial cannula 86 in the aorta, a venous cannula 92 in the inferior vena cava, and another venous cannula 93 in the superior vena cava or, alternatively, a venous cannula in the atrium. These cannulas 86, 89, 92 and 93 engage or are snapped into the cannula slots 56 and are advantageously held in position so as not to obstruct the surgeon's access to the heart. The cannulas 86, 89, 92 and 93 are also secured in the tissue of the cardiovascular components using purse-string sutures which are held by choker grips 62 mounted on the instrument platform 50.

A retrograde cardioplegia catheter 91 is also placed in the heart and secured in position with purse-string sutures held in position by a choker mounted on the instrument platform 50. The retrograde cardioplegia catheter 91 is also snapped into a cannula slot 56 and held in position so as not to obstruct the surgeon's access to the heart. Optionally, a malleable suction cannula or light tube 90 may be snapped into one of the cannula slots 56 to assist in the surgical procedure.

Once CPB is established, a cardioplegic solution is infused in the heart to arrest the heart. With the heart arrested, and in the case of a left-sided mini-thoracotomy, an atriotomy of the left atrium is performed to expose the mitral valve. However, in the case of a right-sided mini-thoracotomy, an atriotomy of the right atrium is performed and then an incision is made through the septum to access the left atrium and expose the mitral valve. An atrial retractor used to retract the atriotomy and other tissue, is extended into the heart on the end of a handle 88 that engages a mount on the instrument platform 50 with a connector 94.

Next, the mitral valve is excised, in whole or in part, and sutures are placed in the annulus. The sutures are held in position and organized by suture grips 58 on the surface of the instrument platform 50 or on the housing 66 of the suture spools 64. A valve prosthesis 77 mounted on a valve holder 78 which is connected to the instrument platform 50, is then positioned adjacent the annulus and the sutures are placed in the cuff or valve mounting mechanism of the valve prosthesis 77. With the sutures placed in the cuff, the valve 77 is seated and the sutures are tied to secure the valve 77 in place. With the valve 77 secured, the atriotomy is closed, the heart is vented and resuscitated, the cannulas and catheters are removed, the corresponding incisions are closed, and the pericardial opening is closed. The instrument platform 50 is then removed and the spreader mechanism 30 of the retractor 10 is attached to the blade arms 16 and 18 to close the blades 12 and 14. Once in a closed position, the blades are removed and the thoracotomy is closed.

Alternate embodiments of an instrument platform 150 and a wound retractor 110 of the present invention are shown in FIGS. 7–9. Referring to FIG. 7, the instrument platform 150 is shown mounted on the wound retractor 110. The body 152 of the instrument platform 150 has a generally planar upper surface with generally curved edges or sidewalls extending downwardly therefrom. In addition, the platform body is shown to include a plurality of cannula notches 156 formed therein to secure cannulas during a surgical procedure. As with the instrument platform 50 discussed above, the platform body 152 of the instrument platform 150 also includes instrument mounts 154 and suture grips (not shown) formed therein.

Referring to FIG. 9, the retractor 110 is shown to include a pair of blades 112 and 114 having blade mounts 121 and 120 extending upwardly therefrom. A spreader mechanism 130 is interconnected to the blade mounts 121 and 120 via blade arms 116, 117, 118 and 119. The blade arms 116, 117, 118 and 119 are connected at a first end to a scissor mechanism (not shown) of the spreader mechanism 130 and are pivotally connected to the blade mounts 120 and 121 at pivots 122, 123, 124 and 125, respectively. Bosses 147 and 149 extend upwardly from the blades 112 and 114 to snap into a recess or receptacle (not shown) on the underside of the instrument platform 150 to mount the instrument platform on the retractor 110.

Referring to FIGS. 7 and 8, the spreader mechanism includes a drive shaft 133 with a detachable actuator knob 132. The actuator knob 132 is detachably mounted on the drive shaft 133 with a ball-and-socket type mechanism. A push-button (not shown) in the end of the actuator knob 132 is actuated to force a piston 137 that is slidably received in the drive shaft 133 away from the end of the shaft where the actuator knob 132. As the piston 137 recesses in the shaft 133, the balls 135 recess into the drive shaft 133 to release the knob 132 from the shaft 133.

In operation, the actuator knob 132 is mounted on the drive shaft 133 of the retractor 110. The blades 112 and 114 are secured in a surgical incision. The actuator knob 132 is then rotated to cause the blades 112 and 114 of the retractor 110 to spread apart to a desired opening. The instrument platform 150 is then mounted on the retractor 110 and a desired surgical procedure is then performed.

While the above description contains many specificities, these should not be construed as limitations on the scope of the invention, but rather as an exemplification of a preferred embodiment thereof. Other variations are possible.

Accordingly, the scope of the present invention should be determined not by the embodiments illustrated above, but by the appended claims and their legal equivalents.

What is claimed is:

1. An instrument platform for surgical procedures, comprising
    a platform body having a central opening formed therein for access to a surgical incision;
    a plurality of notches formed in said platform body, each of said plurality of notches being shaped to releasably retain a surgical instrument therein;
    a plurality of instrument mounts formed on said platform body; and
    a plurality of suture grips formed in said platform body.
2. The instrument platform of claim 1 wherein each of said plurality of suture grips comprises
    a canyon portion for locating said suture grips, and
    a slot portion for securing a suture.
3. The instrument platform of claim 1 further comprising a suture choker engaging one of said plurality of suture grips.
4. The instrument platform of claim 1 wherein said platform is constructed of injected molded plastic.
5. An instrument platform assembly for surgical procedures comprising
    a retractor, and
    an instrument platform mounted on said retractor, said instrument platform having a platform body with a central opening and a plurality of instrument slots shaped to releasably retain a surgical instrument therein.

6. The instrument platform assembly of claim 5 wherein said retractor comprises
a spreader mechanism,
first and second blade arms connected to said spreader mechanism, and
first and second blades connected to said first and second blade arms.

7. The instrument platform assembly of claim 6 wherein said first and second blades are detachable from said first and second blade arms.

8. The instrument platform assembly of claim 6 wherein said spreader mechanism is detachable from said first and second blade arms.

9. The instrument platform assembly of claim 5 wherein said platform body further comprises a plurality of instrument mounts formed thereon.

10. The instrument platform assembly of claim 9 further comprising a suture spool engaging one of said plurality of instrument mounts on said platform body.

11. The instrument platform assembly of claim 5 wherein said platform body further comprises a plurality of suture grips formed therein.

12. The instrument platform assembly of claim 11 wherein each of said plurality of said suture grips comprises first and second elongated V-notches wherein said first V-notch is larger than said second V-notch.

13. The instrument platform assembly of claim 11 further comprising a suture choker engaging one of said plurality of suture grips.

14. The instrument platform assembly of claim 5 further comprising a cannula secured in at least one of said plurality of instrument slots.

15. A method of cardiovascular surgery comprising the steps of
opening the thoracic cavity of a patient with a wound retractor,
mounting an instrument platform on said retractor, said instrument platform comprising a platform body having a central opening and a plurality of cannula notches and a plurality of suture grips formed in said platform body,
opening the pericardium to expose the patient's heart,
cannulating the patient's heart for cardiopulmonary bypass and cardioplegia delivery, and
securing the cannulae for cardiopulmonary bypass and cardioplegia delivery in said cannula notches of said platform body.

16. The method of claim 15 wherein said retractor includes first and second blade arms, a spreader mechanism detachably coupled to said first and second blade arms, and first and second blades detachably coupled to said first and second blade arms, further comprising the step of detaching the spreader mechanism from said first and second blade arms once a desired opening is created in the thoracic cavity.

17. The method of claim 16 further comprising the steps of
attaching the spreader mechanism to a second wound retractor,
creating a second opening in the thoracic cavity with the second wound retractor,
removing the instrument platform from the wound retractor, and
mounting the instrument platform on the second wound retractor.

18. The method of claim 15 further comprising the steps of
attaching sutures to the edges of the pericardial opening, and
fixing said sutures to said suture grips on said platform body.

19. The method of claim 15 further comprising the steps of placing purse string sutures in the tissue of a cardiovascular member,
piercing a hole in the tissue of the cardiovascular member in an area surrounded by the purse string sutures,
placing a cannula in the cardiovascular member through the pierced hole,
placing the ends of a purse string suture through a suture choker, fixing the choker and the purse string suture in a suture grip on the platform body, and
cinching the purse string suture to fix and seal the cannula in place in the cardiovascular member.

20. The method of claim 15 further comprising the steps of
exposing a cardiac valve,
excising said cardiac valve,
placing a plurality of sutures in an annulus of said cardiac valve, and
fixing said plurality of sutures in said plurality of suture grips in said platform body.

21. The method of claim 20 further comprising the steps of
placing the plurality of sutures in a cuff of a valve prosthesis,
seating said valve prosthesis in said annulus, and
tying said plurality of sutures to secure said valve prosthesis.

22. The method of claim 21 further comprising the steps of
establishing cardiopulmonary bypass, and
arresting the patient's heart.

23. The method of claim 22 further comprising the steps of
venting the heart,
resuscitating the heart,
removing the cannulas, and
removing the wound retractor and instrument platform.

24. A method of surgery comprising the steps of
making an incision in a patient's body,
creating an opening with a wound retractor,
mounting an instrument platform on said retractor, and
securing sutures, surgical instruments and cannulas to said instrument platform.

25. An instrument platform for surgical procedures, comprising
a platform body having a central opening formed therein for access to a surgical incision;
a plurality of notches formed in said platform body, each of said plurality of notches being shaped to releasably retain a surgical instrument therein;
a plurality of instrument mounts formed on said platform body; and
a suture spool engaging at least one of said mounts on said platform body.

26. The instrument platform of claim 25 wherein said suture spool comprises
a housing mountable to said platform body,
a spool member mounted in said housing,
a needle slot formed in said housing, and
a suture having a needle attached to one end and being wound about said spool member.

27. An instrument platform for surgical procedures, comprising
   a platform body having a central opening formed therein for access to a surgical incision;
   a plurality of notches formed in said platform body, each of said plurality of notches being shaped to releasably retain a surgical instrument therein;
   a plurality of instrument mounts formed on said platform body; and
   a cannula secured in one of said plurality of notches in said platform.

28. An instrument platform for surgical procedures, comprising
   a platform body having a central opening formed therein for access to a surgical incision;
   a plurality of notches formed in said platform body, each of said plurality of notches being shaped to releasably retain a surgical instrument therein; and
   herein said platform body includes a generally curvalinear cross-sectional shape for creating a space between a patient's chest and said platform body adjacent to said central opening.

29. An instrument platform for surgical procedures, comprising
   a platform body having a central opening formed therein for access to a surgical incision;
   a plurality of notches formed in said platform body, each of said plurality of notches being shaped to releasably retain a surgical instrument therein; and
   wherein said platform body is mountable to a reactor.

30. An instrument platform for surgical procedures, comprising a platform body having a central opening formed therein for access to a surgical incision;
   a plurality of notches formed in said platform body, each of said plurality of notches being shaped to releasably retain a surgical instrument therein;
   a plurality of instrument mounts formed on said platform body; and
   a valve holder engaging one of said plurality of said instrument mounts.

31. An instrument platform body for surgical procedures mountable to a retractor, comprising
   a platform body having a central opening formed therein for access to a surgical incision;
   a plurality of notches formed in said platform body, each of said plurality of notches being shaped to releasably retain a surgical instrument therein.

32. The instrument platform of claim 31 further comprising a plurality of instrument mounts formed on said platform body.

33. The instrument platform of claim 31 wherein said platform body is constructed of injected molded plastic.

* * * * *